US009651515B2

(12) United States Patent
Wang et al.

(10) Patent No.: US 9,651,515 B2
(45) Date of Patent: May 16, 2017

(54) BIOSENSOR, MANUFACTURING METHOD OF BIOSENSOR AND METHOD OF DETECTING OBJECT

(71) Applicant: NATIONAL TSING HUA UNIVERSITY, Hsinchu (TW)

(72) Inventors: Yu-Lin Wang, Hsinchu (TW); Kuan-Chung Fang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 219 days.

(21) Appl. No.: 14/308,746

(22) Filed: Jun. 19, 2014

(65) Prior Publication Data

US 2015/0241376 A1 Aug. 27, 2015

(30) Foreign Application Priority Data

Feb. 27, 2014 (TW) .............................. 103106717 A

(51) Int. Cl.
*G01N 27/327* (2006.01)

(52) U.S. Cl.
CPC .... *G01N 27/3272* (2013.01); *Y10T 29/49155* (2015.01)

(58) Field of Classification Search
CPC .............................. G01N 27/327; Y10T 29/491
See application file for complete search history.

(56) References Cited

U.S. PATENT DOCUMENTS

| | | | | |
|---|---|---|---|---|
| 2003/0062263 A1* | 4/2003 | Stanford | ................ | C12Q 1/001 204/403.01 |
| 2011/0297556 A1* | 12/2011 | Unwin | ................ | G01N 27/308 205/792 |
| 2011/0303554 A1* | 12/2011 | Oguchi | ................ | C12Q 1/005 205/688 |
| 2012/0148449 A1 | 6/2012 | Chuang et al. | | |
| 2013/0001090 A1* | 1/2013 | Rubinson | ................ | A61N 1/04 205/118 |

FOREIGN PATENT DOCUMENTS

TW 201224453 A1 6/2012

OTHER PUBLICATIONS

Peroxisomes, Encyclopedia of Biological Chemistry, vol. 3. q 2004.*
Song, Journal of the Korean Physical Society, vol. 54, No. 4, Apr. 2009, pp. 1612_1618.*
Kuan-Chung Fang, et al., "Realization of an ultra-sensitive hydrogen peroxide sensor with conductance change of horseradish peroxidase-immobilized polyaniline and investigation of the sensing mechanism", Biosensors and Bioelectronics, 55 (2014) 294-300, Dec. 31, 2013, http://dx/doi.org/10.1016/j.bios.2013.12.029.

* cited by examiner

*Primary Examiner* — Jennifer Dieterle
(74) *Attorney, Agent, or Firm* — Li & Cai Intellectual Property (USA) Office

(57) ABSTRACT

A biosensor includes a substrate, an electrode layer, a conductive polymer layer and a bio-recognizing element. The electrode layer is disposed on the substrate. The conductive polymer layer is disposed on the electrode layer and partially covers the substrate. The bio-recognizing element is disposed on the conductive polymer layer. A chemical reaction takes place between the object and the bio-recognizing element, and the chemical reaction decreases the conductivity of the conductive polymer layer.

3 Claims, 2 Drawing Sheets

BIOSENSOR, MANUFACTURING METHOD OF BIOSENSOR AND METHOD OF DETECTING OBJECT

BACKGROUND

1. Technical Field

The present disclosure relates to a biosensor, a method of detecting an object material through the biosensor and method of manufacturing the biosensor.

2. Description of Related Art

Currently, the common biosensor is used to measure the concentration of an object material. Generally speaking, the common biosensor usually uses bio-recognizing element, such as enzyme, antibody or DNA to react with the object material so as to measure the concentration of the object material. Notably, since the bio-recognizing element is highly specific for the object material, the bio-recognizing element can react with the special object material.

Specifically, the conventional biosensor usually measures the concentration of the object material through electro-chemical analysis or fluorescence analysis. In the conventional measuring method of the concentration of the object material, most of the emphases are on the modification of the electrochemical method, or to enhance the color recognition of the fluorescent method. However, the manufacturing method of the conventional biosensor and the conventional measuring method of the object material are complicated.

SUMMARY

An embodiment of the present disclosure provides a biosensor which is used to measure the concentration of an object material in an analyte.

An embodiment of the present disclosure provides a biosensor. The biosensor includes substrate, an electrode layer, a conductive polymer layer and a bio-recognizing element. The electrode layer is disposed on the substrate. The conductive polymer layer is disposed on the electrode layer and partially covers the substrate. The bio-recognizing element is disposed on the conductive polymer layer. A chemical reaction takes place between the object and the bio-recognizing element, and the chemical reaction decreases the conductivity of the conductive polymer layer.

An embodiment of the present disclosure provides a manufacturing method of a biosensor to fabricate the biosensor.

An embodiment of the present disclosure provides a manufacturing method of a biosensor. The electrode layer is disposed on the substrate. The conductive polymer layer is disposed on the electrode layer. The bio-recognizing element is disposed on the conductive polymer layer.

An embodiment of the present disclosure provides a method of detecting an object material to measure the concentration of the object material. The analyte having object material is in contact with the bio-recognizing element disposed on the conductive polymer layer, and the conductivity variation of the conductive polymer layer is measured through the electrode layer.

In summary, the present disclosure provides a biosensor, a manufacturing method of the biosensor, and a method of detecting an object material. The biosensor is used to measure concentration of the object material in an analyte. The biosensor includes the substrate, the electrode layer, the conductive polymer layer and the bio-recognizing element. The electrode layer is disposed on the substrate. The conductive polymer layer is disposed on the electrode layer. The bio-recognizing element is disposed on the conductive polymer layer. The analyte having object material is in contact with the bio-recognizing element disposed on the conductive polymer layer, and the conductivity variation of the conductive polymer layer is measured through the electrode layer.

Compared with conventional technology, the manufacturing method of the biosensor is simple, the manufacturing cost of the biosensor is lower, and the accuracy of measurement of the biosensor is higher. In addition, the measuring method of the object material is simple, and the concentration of the object material can be measured without the need of using electro-chemical analysis.

In order to further understand the techniques, means and effects of the present disclosure, the following detailed descriptions and appended drawings are hereby referred, such that, through which, the features and aspects of the present disclosure can be thoroughly and concretely appreciated; however, the appended drawings are merely provided for reference and illustration, without any intention to be used for limiting the present disclosure.

BRIEF DESCRIPTION OF THE DRAWINGS

The accompanying drawings are included to facilitate further understanding of the present disclosure, and are incorporated in and constitute a part of this specification. The drawings illustrate exemplary embodiments of the present disclosure and, together with the description, serve to explain the principles of the present disclosure.

DESCRIPTION OF THE EXEMPLARY EMBODIMENTS

Figure 1:
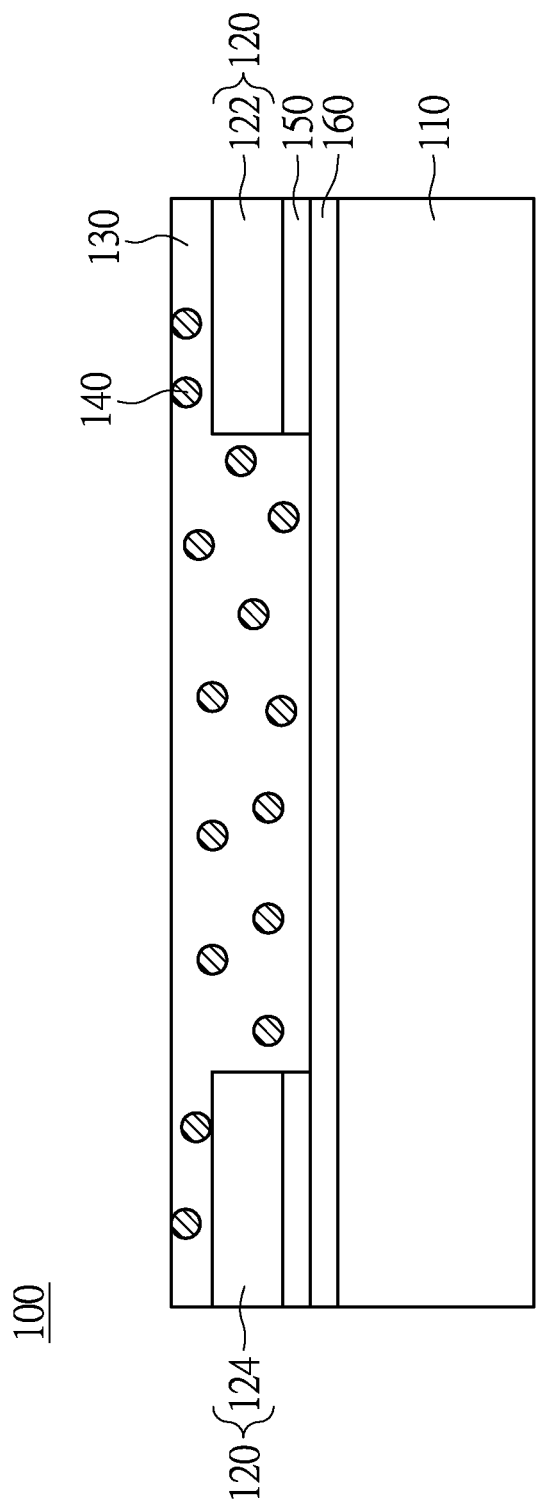
FIG. 1 depicts a structure schematic diagram of a biosensor in accordance with a first embodiment of the present disclosure.

FIG. 1 illustrates a structure schematic diagram of a biosensor in accordance with a first embodiment of the present disclosure. Please refer to FIG. 1. The biosensor 100 is used to measure the concentration of an object material in an analyte. The biosensor 100 includes a substrate 110, an electrode layer 120, a conductive polymer layer 130 and a bio-recognizing element 140. The electrode layer 120 is disposed on the substrate 110, and the conductive polymer layer 130 is disposed on the electrode layer 120. The bio-recognizing element 140 is disposed on the conductive polymer layer 130.

The substrate 110 is used as a carrier for the electrode layer 120 and the conductive polymer layer 130. The substrate 110 is made of insulating material such as silicon, glass, ceramics, plastic or the like. In the present embodiment, the substrate 110 is a silicon substrate. However, the material of the substrate 110 is not limited to the examples provided herein.

The electrode layer 120 is disposed on the substrate 110, and includes a positive electrode 122 and a negative electrode 124. There exists a distance between the positive electrode 122 and the negative electrode 124. In practice, the electrode layer 120 is used to output electrical signal of the conductive polymer layer 130. The electrode layer 120 is made of conductive material such as gold, silver, copper or the like. In particular, in the present embodiment, the electrode layer 120 is made of gold due to gold's good conductivity and biological compatibility. However, the material of the electrode layer 120 is not limited to the examples provided herein.

The conductive polymer layer 130 is disposed on the electrode layer 120 and partially covers the substrate 110. Namely, the conductive polymer layer 130 covers not only the positive electrode 122 and the negative electrode 124, but also the surface between the positive electrode 122 and the negative electrode 124. In this present embodiment, the conductive polymer layer 130 is made of polyaniline (PAn). However, in other embodiment, the conductive polymer layer 130 can be made of other material such as Polypyrrole (PYy), or Polythiophene (PTh). The material of the conductive polymer layer 130 is not limited to the examples provided herein.

The bio-recognizing element 140 is disposed on the conductive polymer layer 130 and is peroxisome. The conductive polymer layer 130 is used as a carrier of bio-recognizing element 140 so that the conductive polymer layer 130 can fix the bio-recognizing element 140 and enhance the stability of the bio-recognizing element 140.

In order to make the electrode layer 120 attached to the substrate 110 preferably, the biosensor 100 can further include an adhesive layer 150. The adhesive layer 150 can be disposed on the substrate 110, and the electrode layer 120 can be disposed on the adhesive layer 150. It is worth mentioning that the adhesive layer 150 is mainly used to enhance the adhesion of the electrode layer 120 on the substrate 110. In the present embodiment, the adhesive layer 150 is made of titanium (Ti). However, in other embodiment, the adhesive layer 150 can be made of other metal or alloy such as tantalum (Ta), TiW alloy or the like.

In addition, the biosensor 100 can further include an insulating layer 160. The insulating layer 160 is disposed between the substrate 110 and the adhesive layer 150, and the insulating layer 160 is in contact with the substrate 110. The insulating layer 160 is used to reduce the stress between the electrode layer 120 and the substrate 110. In the present embodiment, the insulating layer 160 is made of silicon nitride ($Si_3N_4$). However, the material of the insulating layer 160 is not limited to the examples provided herein.

Figure 2:
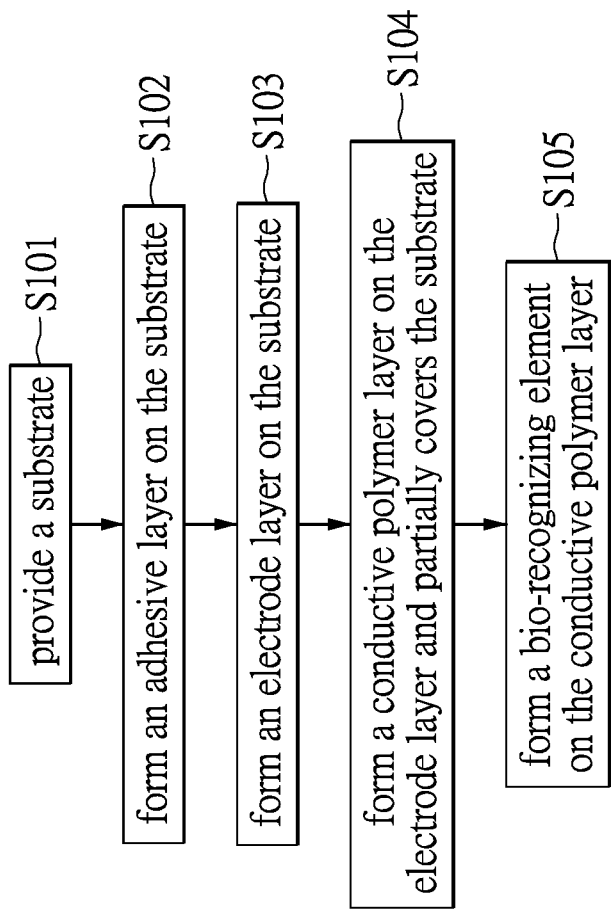
FIG. 2 is a flowchart depicting manufacturing method of a biosensor in accordance with a first embodiment of the present disclosure.

FIG. 2 is a flowchart depicting manufacturing method of a biosensor in accordance with a first embodiment of the present disclosure. Please refer to FIG. 2. In the step S101, the substrate 110 is provided, such as silicon substrate, glass substrate, ceramics substrate, plastic substrate or the like. In the present embodiment, the substrate 110 is a silicon substrate. However, the material of the substrate 110 is not limited to the examples provided herein.

Notably, in the present embodiment, the biosensor 100 can further include an insulating layer 160 formed on the surface of the substrate 110 through chemical vapor deposition (CVD). The insulating layer 160 is made of silicon nitride ($Si_3N_4$). However, the process and material of the insulating layer 160 are not limited to the examples provided herein. In addition, in other embodiment, the biosensor 100 may not include the insulating layer 160.

In the step S102, the adhesive layer 150 is formed on the substrate 110. Specifically, in the present embodiment, the adhesive layer 150 is formed by sputtering a Ti film on the surface of the insulating layer 160 so as to enhance the adhesion of the electrode layer 120 in the follow-up process. However, in other embodiment, the biosensor 100 may not include the insulating layer 160, and then the adhesive layer 150 can be directly deposited on the surface of the substrate 110.

In particular, in other embodiment, the adhesive layer 150 can be made of other metal or alloy such as tantalum (Ta), TiW alloy or the like. The process and material of the adhesive layer 150 are not limited to the examples provided herein.

In the step S103, the electrode layer 120 is formed on the substrate 110. In practice, the electrode layer 120 is a conductive film formed by spray-coating, ion-plating, sputter depositing, evaporation depositing or the like. In the present embodiment, the electrode layer 120 is made of gold. However, the process and material of the electrode layer 120 is not limited to the examples provided herein.

In the step S104, the conductive polymer layer 130 is formed on the electrode layer 120 and partially covers the substrate 110. Specifically, a precursor solution is formed by mixing 0.2 to 0.3 grams polyaniline emeraldine base (EB) powder and 4.5 to 5.5 milliliter dimethyl sulfoxide (DMSO). In one preferred embodiment, the precursor solution is formed by mixing 0.3 grams polyaniline emeraldine base (EB) powder and 5 milliliter dimethyl sulfoxide (DMSO). Then, a polyaniline solution is formed by mixing the precursor solution and an acid solution, such as hydrochloric acid solution, nitric acid solution, and sulfuric acid solution. The polyaniline solution coats the electrode layer 120 and the substrate 110. Subsequently, a baking process is performed to form a polyaniline film covering the electrode layer 120 and the substrate 110. In one preferred embodiment, the sulfuric acid solution is adapted to enhance the conductance and stability of the polyaniline film. The polyaniline film covers not only the positive electrode 122 and the negative electrode 124, but also the surface of the substrate 110 between the positive electrode 122 and the negative electrode 124. Notably, the temperature of the baking process is between 50° C. and 60° C., and the time period of the baking process is between 15 and 30 minutes. In another embodiment, the temperature of the baking process is 60° C., and the time period of the baking process is 20 minutes.

After forming the polyaniline film on the substrate 110, the polyaniline film is transformed from emeraldine (EB) state to leucoemeraldine (LE) state by applying voltage between 0.1 volts to 0.25 volts for 10 minutes on the polyaniline film, and then the polyaniline film is washed with deionized water. Preferably, the voltage is 0.2 volts. Subsequently, the substrate 110 with the polyaniline film is immersed in sodium hydroxide solution, and then dried with nitrogen. Thereafter, the 1,3-propane sultone is dropped to the polyaniline film.

In the step S105, the bio-recognizing element 140 is formed on conductive polymer layer 130. Specifically, the bio-recognizing element 140 and a buffer solution are mixed first, and then diaminobenzidine (DAB) is added in so as to form a bio-recognizing element solution. The diaminobenzidine is used to be a chromogenic substrate. In particular, the bio-recognizing element 140 is peroxisome. The substrate 110 with the polyaniline film is immersed in the bio-recognizing element solution for 20 minutes. Subsequently, the polyaniline film is applied voltage at 0.4 volts for 4 minutes to make the peroxisome stick on the polyaniline film. Subsequently, the polyaniline film is washed with deionized water, and then dried with nitrogen. Hence, the biosensor 100 is finished substantially.

In particular, while the biosensor 100 is prepared, an analyte having object material is in contact with the bio-recognizing element 140 disposed on the conductive polymer layer 130. At that instant, the object material and the bio-recognizing element 140 produce a chemical reaction, such as oxidation-reduction reaction. When the bio-recognizing element 140 is oxidized by the object material, the bio-recognizing element 140 grabs electrons from the conductive polymer layer 130. Hence the conductivity of the conductive polymer layer decreases. Thereafter, the conductivity variation of the conductive polymer layer 130 measured through the electrode layer 120 is an indicator of the concentration of the object material.

It is worth mentioning that the bio-recognizing element 140 is reduced after accepting electrons from the conductive polymer layer 130. Hence, the bio-recognizing element 140 can react with other object material which is remained in the analyte.

For instance, in one embodiment, while the object material needed to be measured is hydrogen peroxide, the bio-recognizing element 140 is peroxisome. The hydrogen peroxide in the analyte and the peroxisome in the conductive polymer layer 130 produce a chemical reaction when they are in contact with each other. When the peroxisome is oxidized by the hydrogen peroxide, the peroxisome grabs electrons from the conductive polymer layer 130. Hence the conductivity of the conductive polymer layer decreases. Thereafter, the concentration of hydrogen peroxide, namely the object material, can be obtained by measuring the conductivity variation of the conductive polymer layer 130 through the electrode layer 120.

In other embodiment, while measuring other object material, the biosensor 100 may be added another bio-recognizing element 140. Specifically, while the object material needed to be measured is glucose, the bio-recognizing element 140 in the conductive polymer layer 130 is peroxisome and glucose oxidase (GOD). The glucose oxidase reacts with the glucose to generate hydrogen peroxide, and the hydrogen peroxide can reacts with the peroxisome. In the same way, when the peroxisome is oxidized by the hydrogen peroxide, the peroxisome grabs electrons from the conductive polymer layer 130. Hence the conductivity of the conductive polymer layer decreases. Thereafter, the concentration of hydrogen peroxide, namely the object material, can be obtained by measuring the conductivity variation of the conductive polymer layer 130 through the electrode layer 120.

Notably, the larger the conductivity variation of the conductive polymer layer 130 is, the higher the concentration of the object material is. Namely, the larger the conductivity variation of the conductive polymer layer 130 of the biosensor 100 is measured, the higher the concentration of the object material is. When the bio-recognizing element 140 is peroxisome, the concentration of the hydrogen peroxide measured by the biosensor 100 is between 0.7 micro-molar ($\mu M$) and 1 micro-molar ($\mu M$). Therefore, compared with conventional technology, the manufacturing method of the biosensor 100 is simple. In addition, the measuring method of an object material can be used to measure the concentration of the hydrogen peroxide without the need for measuring through electro-chemical analysis, such as cyclic voltammetry.

In summary, the present disclosure provides a biosensor, a manufacturing method of the biosensor, and a measuring method of an object material. The biosensor can measure concentration of the object material in an analyte. The biosensor includes the substrate, the electrode layer, the conductive polymer layer and the bio-recognizing element. The electrode layer is disposed on the substrate. The conductive polymer layer is disposed on the electrode layer. The bio-recognizing element is disposed on the conductive polymer layer. The analyte having object material is in contact with the bio-recognizing element disposed on the conductive polymer layer, and the conductivity variation of the conductive polymer layer is measured through the electrode layer.

Compared with conventional technology, the manufacturing method of the biosensor is simple, the manufacturing cost of the biosensor is lower, and the accuracy of measurement of the biosensor is higher. In addition, the method for detecting the object material is simple, and the concentration of the hydrogen peroxide can be measured without the need for measuring through electro-chemical analysis.

The above-mentioned descriptions represent merely the exemplary embodiment of the present disclosure, without any intention to limit the scope of the present disclosure thereto. Various equivalent changes, alternations or modifications based on the claims of present disclosure are all consequently viewed as being embraced by the scope of the present disclosure.

What is claimed is:

1. A biosensor used to measure concentration of an object material in an analyte comprising:
    a substrate;
    an electrode layer disposed on the substrate;
    an insulating layer disposed between the substrate and the electrode layer;
    a conductive polymer layer disposed on the electrode layer and partially covers the substrate; and
    a bio-recognizing element disposed on the conductive polymer layer, wherein the object material and the bio-recognizing element produce a chemical reaction for decreasing the conductivity of the conductive polymer layer,
    wherein the bio-recognizing element is peroxisome or the combination of peroxisome and glucose oxidase.

2. The biosensor according to claim 1, wherein the biosensor further comprises an adhesive layer disposed between the insulating layer and the electrode layer.

3. The biosensor according to claim 1, wherein the conductive polymer layer is made of polyaniline.

* * * * *